United States Patent [19]
Wiedner et al.

[11] Patent Number: 5,890,235
[45] Date of Patent: Apr. 6, 1999

[54] SAFETY GOGGLES, IN PARTICULAR INDUSTRIAL SAFETY GOGGLES

[75] Inventors: Klaus Wiedner, Fürth/Bay; Herbert Nussbickl, Nürnberg; Erich Hegendörfer, Cadolzburg, all of Germany

[73] Assignee: Uvex Arbeitsschutz GmbH, Fürth/Bay, Germany

[21] Appl. No.: 927,458

[22] Filed: Sep. 11, 1997

[30] Foreign Application Priority Data

May 17, 1997 [DE] Germany ............... 197 20 907.6

[51] Int. Cl.$^6$ ........................................ A61F 9/02
[52] U.S. Cl. ............................... 2/431; 2/449
[58] Field of Search ................ 2/426, 427, 430, 2/431, 439, 447, 448, 449, 450

[56] References Cited

U.S. PATENT DOCUMENTS

| | | |
|---|---|---|
| 2,617,100 | 11/1952 | Moeller ........................... 2/447 |
| 3,526,449 | 9/1970 | Bolle et al. ...................... 2/447 |
| 4,726,075 | 2/1988 | Hinrichs ......................... 2/449 |
| 5,016,292 | 5/1991 | Rademacher .................... 2/431 |
| 5,289,592 | 3/1994 | Paivarinta ....................... 2/449 |
| 5,379,464 | 1/1995 | Schleger et al. ................. 2/449 |
| 5,423,092 | 6/1995 | Kawai ............................. 2/447 |
| 5,426,573 | 6/1995 | Riehm ............................ 2/449 |
| 5,608,469 | 3/1997 | Bolle .............................. 2/449 |

FOREIGN PATENT DOCUMENTS 89 02 696   5/1989   Germany .

*Primary Examiner*—John J. Calvert
*Assistant Examiner*—Larry D. Worrell, Jr.
*Attorney, Agent, or Firm*—Browdy and Neimark

[57] ABSTRACT

In safety goggles, in particular industrial safety goggles, comprising a one-piece sight piece, the sight piece having lateral, transparent pieces joined on, forming one piece with the sight piece and extending toward the head of the user, it is provided, with a view to expanding the field of vision and increasing the effect of lateral protection, that the sight piece is rounded at its lateral outer ends and that the lateral pieces have a convexity matching this rounded configuration.

20 Claims, 7 Drawing Sheets

SAFETY GOGGLES, IN PARTICULAR INDUSTRIAL SAFETY GOGGLES

BACKGROUND OF THE INVENTION

1. Field of the Invention

The invention relates to safety goggles, in particular industrial safety goggles, comprising a one-piece sight piece, the sight piece having lateral, transparent pieces joined on, forming one piece with the sight piece and extending toward the head of the user.

2. Background Art

Safety goggles of the generic type are known for instance from DE-U-89 02 696.

In conventional safety goggles of the generic type, the lateral pieces joined on are plane, reaching backward from a substantially straight, vertical breaking line. A drawback of this resides in that the breaking line is situated in the lateral field of vision, which considerably obstructs the view to the side.

Goggles are known, in which the sight piece as a whole is curved so strongly that the lateral ends of the sight piece reach around the face as far as to the user's temples. Sight pieces of this type avoid the break that obstructs the view, but they must have a radius of curvature which conditions a comparatively great maximum distance from the face and is not desirable for optical reasons.

SUMMARY OF THE INVENTION

It is the object of the invention to embody safety goggles of the type mentioned at the outset in such a way that optimal lateral protection of the eyes is attained along with the possibility of an unobstructed view to the side.

According to the invention, this object is attained by the lateral outer ends of the sight piece being rounded and the lateral pieces having a convexity that matches this rounded configuration.

The concept according to the invention deviates from conventional solutions, deliberately accepting a more complicated shape of the injection mold in order to avoid break lines in the lateral end portions of the sight piece. Simultaneously, it is ensured that due to their convexity, the pieces joined on laterally experience considerable static stabilization and particles striking from the side are deflected. Moreover, it is possible to fit the rear edge portions at the user's temples optimally to the contour of his face.

Preferably, the radius of curvature of the lateral pieces joined on is between 1 cm and 3 cm, in particular and favorably it is approximately 2 cm. As far as a radius of curvature is mentioned in the foregoing, this does not mean that the lateral pieces have the same radius of curvature throughout; rather, the lateral pieces can be curved non-spherical, the mentioned radiuses of curvature approximately reflecting only the curvature behavior.

In keeping with another embodiment of the invention it is provided that a frame can be locked into place on the upper side of the sight piece, it being possible to articulate bows to the lateral extreme ends of the frame. In this regard it is preferably provided that snap-in pieces can be snapped in the lateral extreme ends of the frame member and have articulated pieces for the articulation of a bow.

An articulated piece on the side of the bow can be provided with a coupling section to be snap-engaged with a bowed coupling piece.

As a result of this specified modular design it is possible to select the individual components depending on the specific requirements, in particular to provide different bows, and to improve the resistance to bombardment.

Favorably, the bowed coupling pieces are made of a softer plastic material than the remaining parts of the goggles so that some convenience of wearing is achieved. Simultaneously, this softness also helps achieve higher elasticity so that it can be provided that for length adjustment, the bowed coupling pieces have an elongated slot with catching recesses, with which engages a locking projection on the inside of the coupling piece.

The extreme ends of the frame can fit over the snap-in piece in the way of a fork, locking projections and locking grooves being formed on the front of the snap-in piece and on the bottom of the forked section of the lateral ends for inclination adjustment.

The forked sections of the lateral ends can have an upper cover working as a stop.

By advantage, the pivot bearing for the bows can be embodied in such a way that a pivot bearing recess is formed in one of the forked sections and a bearing pin is formed on one side of each snap-in piece, the bearing pin engaging with the pivot bearing recess. To facilitate the snap-in operation, the bearing pin can be bevelled.

Favorably, the upper frame member can have a cover section, which stands out backward toward the face of the user, thus ensuring positive fit on the forehead and preventing drops and particles from penetrating from above.

On its lower side, the upper frame member can have a groove for the upper edge of the sight piece to be inserted. The sight piece can have recesses at its lateral ends, and the upper frame member can be provided with corresponding lateral projections for the sight piece to be fixed.

Favorably, the projections on the upper frame member are disposed to be displaced downward in such a way that when the sight piece is inserted, an inner limiting wall of the groove which receives the upper edge of the sight piece fits over the portion of locking engagement. This creates a sort of a slide lock for the fixing of the sight piece.

In the vicinity of the nose piece of the sight piece, a wire section can be incorporated by injection-molding, the lateral extreme ends extending outwards on both sides of the nose, nose pads or the extremities of a nose loop being placed on these ends. Such a design is per se known from sunglasses or optical glasses, but has so far not been put into practice in one-piece industrial safety glasses. This helps achieve especially high convenience of wearing.

Preferably, the sight piece is spherically curved, having favorable optical properties.

Holes for a holding strap can be formed at the ends of the bows.

Another variant can provide for a nose piece to be applied to the frame by injection-molding.

Yet another variant provides for the sight piece to have plate-type pieces joined on, which extend backward and in which oblong holes are formed that are inclined relative to the horizontal, corresponding locking projections on stems being formed on the inside of the frame, which can be inserted in the oblong holes and fixed by the frame being pivoted, the sight piece having a locking projection centrally and the frame having a catching recess.

Details of the invention will become apparent from the ensuing description of preferred embodiments, taken in conjunction with the drawing.

DESCRIPTION OF THE PREFERRED EMBODIMENTS

Figure 1:
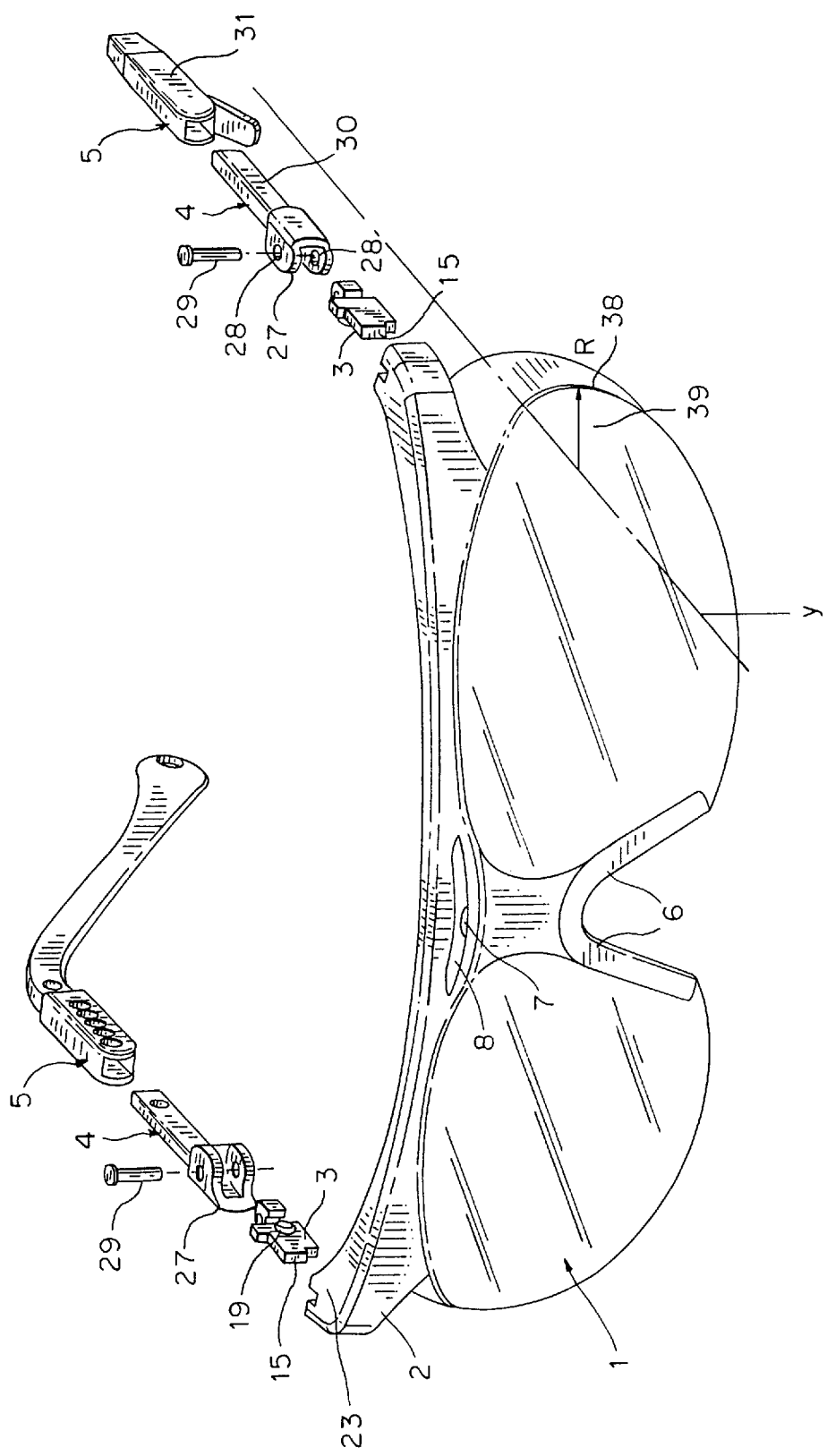
FIG. 1 is an exploded view of goggles according to the invention.

The goggles seen in FIG. 1 comprise a sight piece 1, a frame 2, snap-in pieces 3 to be joined to both sides of the frame pivotally about a horizontal axis, articulated pieces 4 to be joined to the snap-in pieces pivotally about a vertical axis and bowed coupling pieces 5 to be snapped on the articulated pieces 4.

The sight piece 1 is of one-piece structure and in the embodiment seen in FIG. 1, a nose piece 6 is applied to the sight piece by injection-molding.

The frame 2 is locked into place on the sight piece 1. This is put into practice by a locking projection 7 in the middle of the sight piece and a catching recess 8 in the form of an elongated slot in the frame as well as an arresting pin 9' on the frame 2 which reaches over the upper edge 9 of the sight piece 1.

On both sides, the sight piece 1 has retaining incisions 10 and projections 11 formed thereby, which can be inserted in a corresponding slide-lock-type holding arrangement 12 on the sides of the frame 2, the upper edge 9 of the sight piece 1 resting in a groove 13 on the lower side of the frame 2. The inner limiting wall 14 of this groove fits over the sight piece in the holding portion 12 so that the sight piece is fixed inward in the holding portion.

Figure 5:
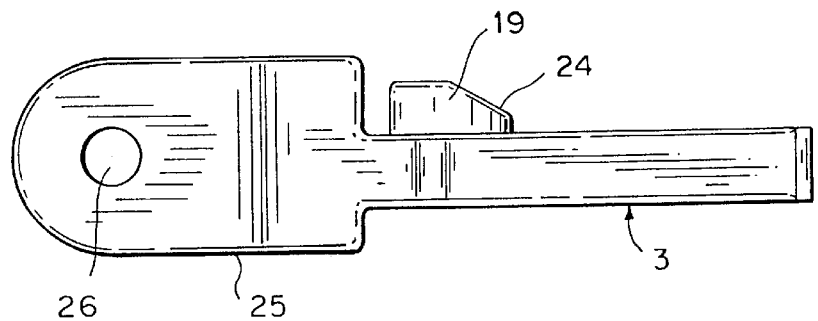
FIG. 5 is a view of the snap-in piece offset by 90° as compared with FIG. 4.
Figure 4:
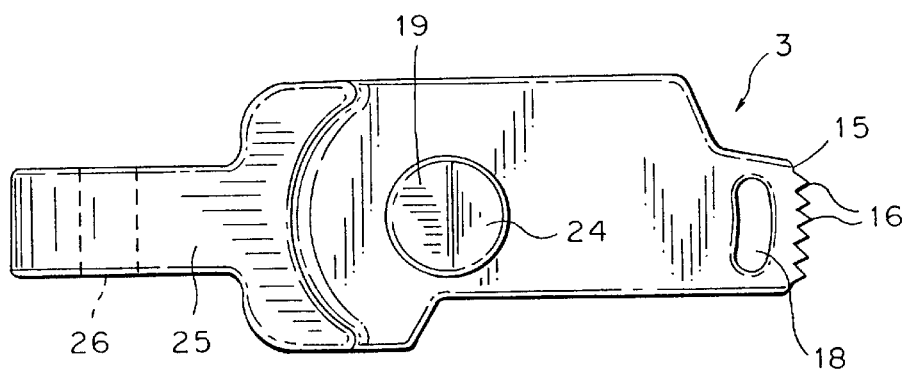
FIG. 4 is an enlarged illustration of a snap-in piece from inside.
Figure 6:
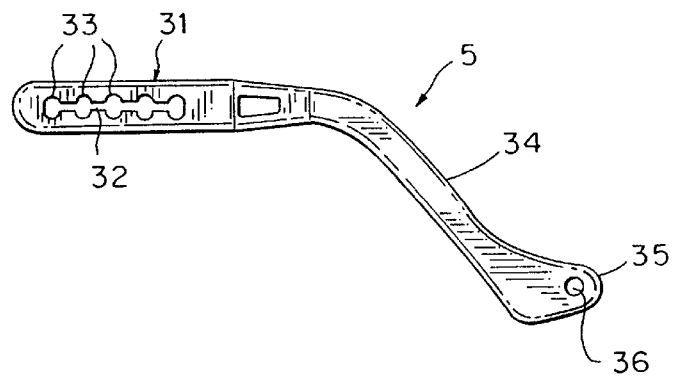
FIG. 6 is a view of the bowed coupling piece.
Figure 7:
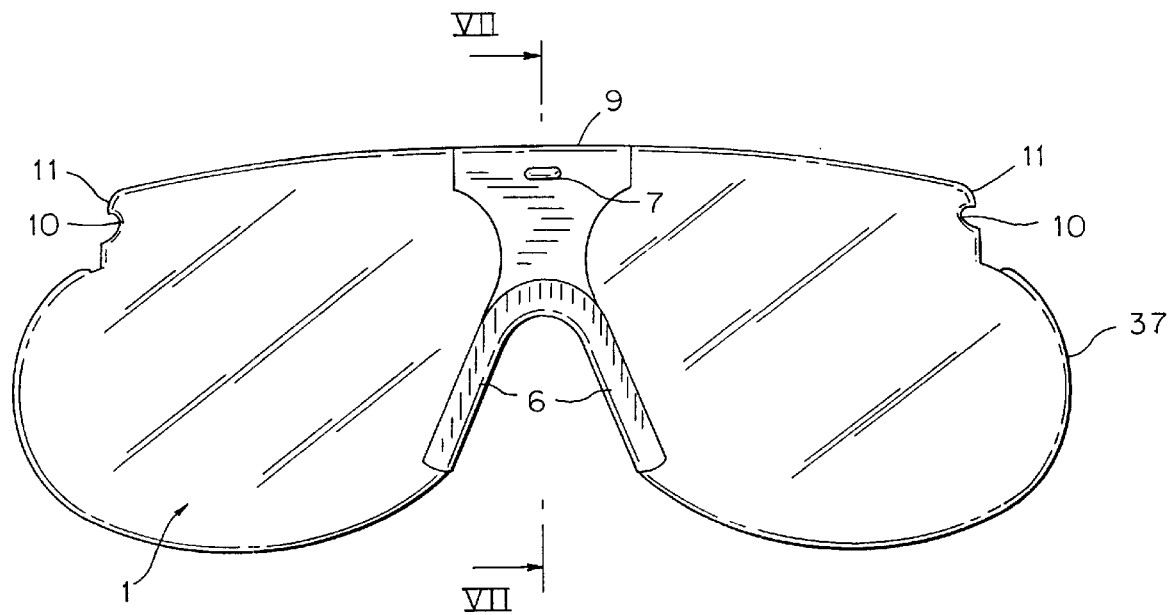
FIG. 7 is a view of the sight piece without the frame.
Figure 8:
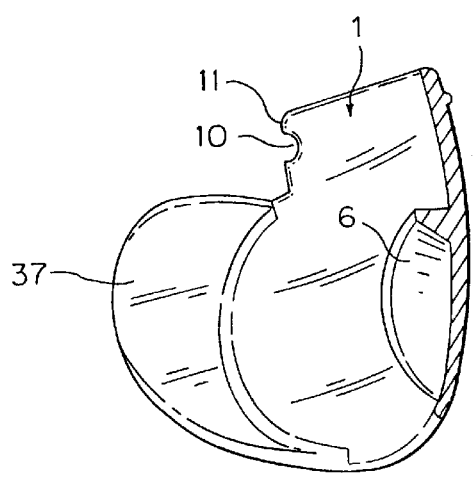
FIG. 8 is a section on the line E—E of FIG. 7.

As seen in particular in FIGS. 4 and 5, the front 15 of each snap-in piece 3 is provided with ribs 16 which cooperate with corresponding ribs 17 on the frame 2, forming an inclination engagement. A recess 18 in the snap-in piece 3 provides for elastic snap-engagement.

A pivot bearing bolt 19 is injection-molded on the inside of the snap-in piece 3. Bolt 19 can be locked into place in corresponding pivot bearing recesses 20 on lateral sections 21 of the frame 2 which extend backward.

Figure 2:
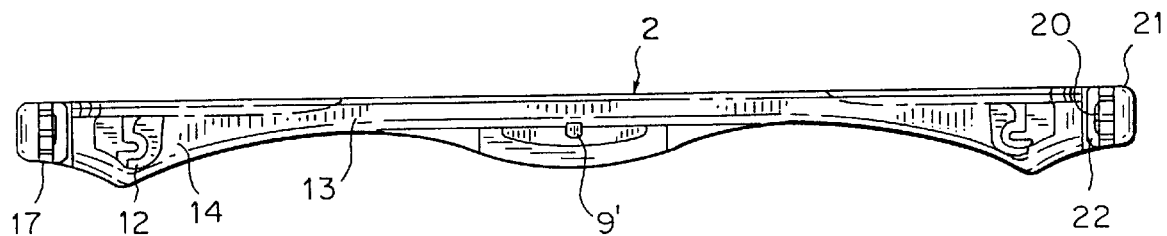
FIG. 2 is a view of the frame from within.
Figure 3:
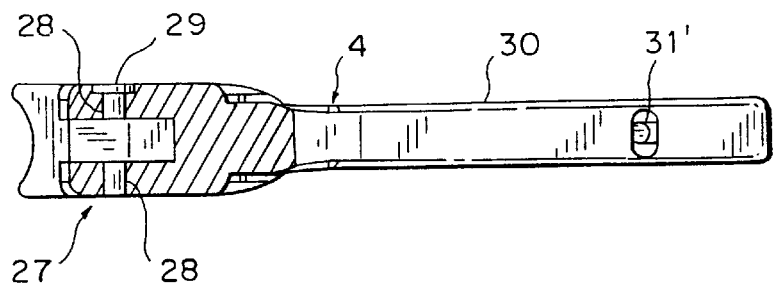
FIG. 3 is a longitudinal section through an articulated piece on an enlarged scale.

In a sectional view, these sections 21 are forked as seen in the view from behind of FIG. 2, the pivot bearing recess 20 being formed in the inner forked section 22.

On their upper side, the forked lateral sections 21 have a cover 23 which prevents any pivoting motion beyond the horizontal position. For the snap-engagement of the pivot bearing bolt 19 with the recess 20 to be facilitated, the pivot bearing bolt 19 is provided with a sloping face 24 (see FIG. 5) in the direction of insertion.

The end of the snap-in piece 3 that is the rear end related to the sight piece 1 comprises a piece joined on 25 which has a pivot bearing hole 26; the latter defines a pivot joint for the bows to be pivoted about a vertical pivot axis, which will be specified below.

The articulated piece 4 also serves to form the pivot joint; as seen in particular in FIG. 1, the articulated piece 4 comprises a forked section 27 which has two pivot bearing holes 28, the forked section 27 fitting over the piece joined on 25 of the snap-in piece 3 from above and below so that the holes 26 and 28 are flush and a tubular rivet 29 can be inserted as a pivot bearing bolt.

The forked section 27 of the articulated piece 4 is followed by a coupling section 30 which has a locking projection 31' on its inside.

The bowed coupling piece 5 comprises a sleeve section 31 into which the coupling section 30 of the articulated piece 4 can be inserted. On the inside of the sleeve section 31, provision is made for an elongated slot 32 with a plurality of catching recesses 33 with which the locking projection 31 can engage, this offering the possibility of length adjustment.

The sleeve section 31 is followed by an ear section 34 which, at its extreme end 35, comprises a hole 36 for a holding strap or the like.

The sight piece 1 is provided with lateral pieces 37 joined on and extending from the outer edge 38 of the sight piece 1 backward toward the face of the user. The edge 38 is rounded along an axis of curvature y which extends in a direction towards the user's head and ears. Edge 38 also has a comparatively narrow radius of curvature R and—not exactly having the shape of a segment of a circle—can be made to converge by such a radius of curvature R. This produces a portion 39 which enlarges the effective width of the sight piece 1 so that the user has a free view to the side that is not obstructed by the vertical edges known from the prior art.

The pieces 37 have a convexity which matches the course of the edge 38 so that high stability of the pieces 37 is obtained, this also protecting against bombardment by particles from outside.

Figure 10:
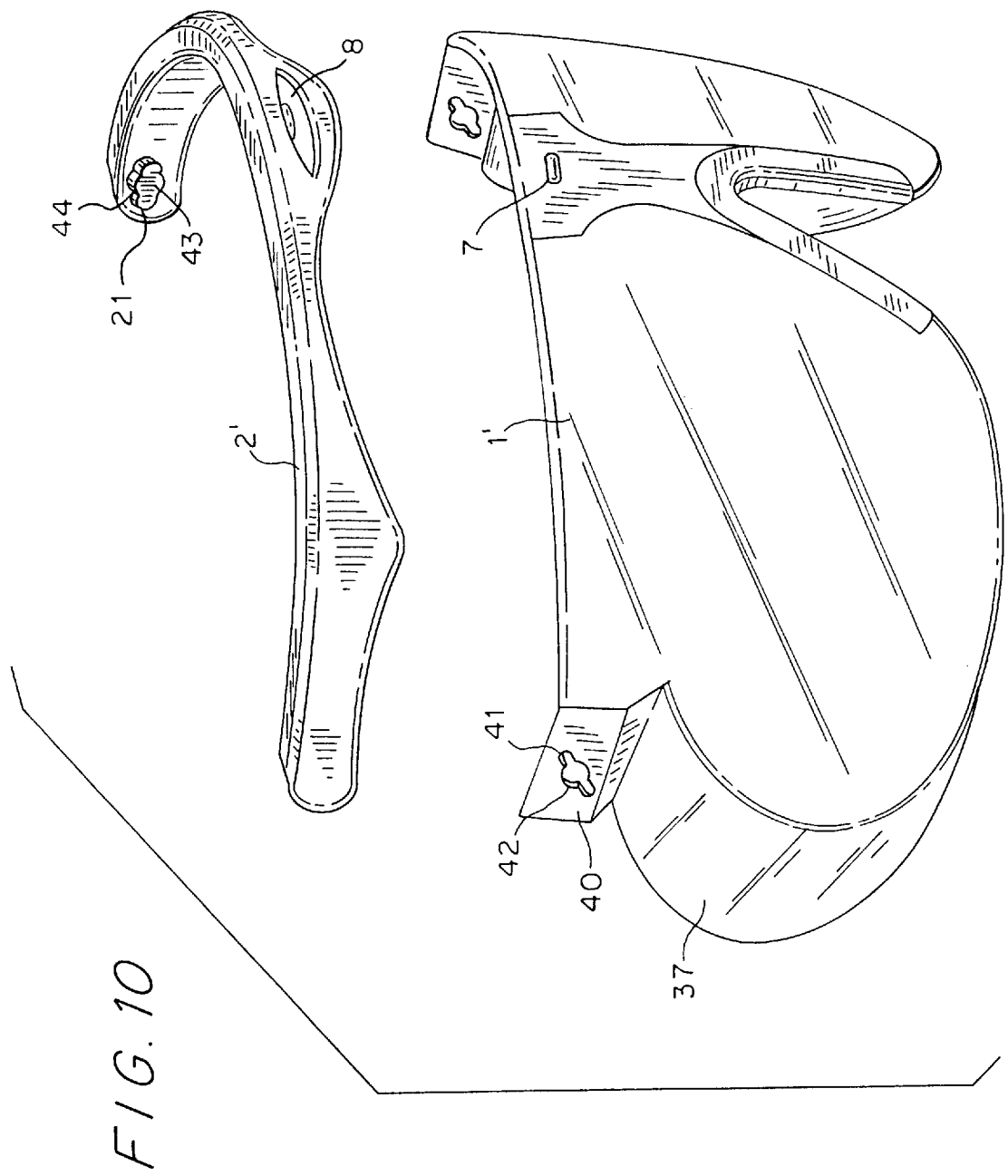
FIG. 10 is a perspective view of the goggles and the frame according to another embodiment.

FIG. 10 illustrates a modified embodiment, in which plate-type pieces 40 are provided above the curved lateral pieces 37, comprising an oblong hole 41 with a central widening 42.

On the inside of the lateral section 21 of the frame member 2', a locking piece 43 is provided, corresponding in shape and having a stem 44 which is horizontal in the plane of the frame member 2', whereas the oblong hole 41 is inclined by approximately 45° relative to the horizontal. Consequently, for fixing, the frame member is placed on the upper side of the sight piece 1', having precisely this inclination, so that the locking pieces 43 pass through the oblong hole; then the front part of the frame 2' is pivoted down, locking engagement taking place in the central portion by means of the locking projection 7 and the catching recess 8. The extreme ends of the frame 2' are arrested, having positive fit, because the locking piece 43 is pivoted relative to the inclined oblong hole 41.

Figure 9:
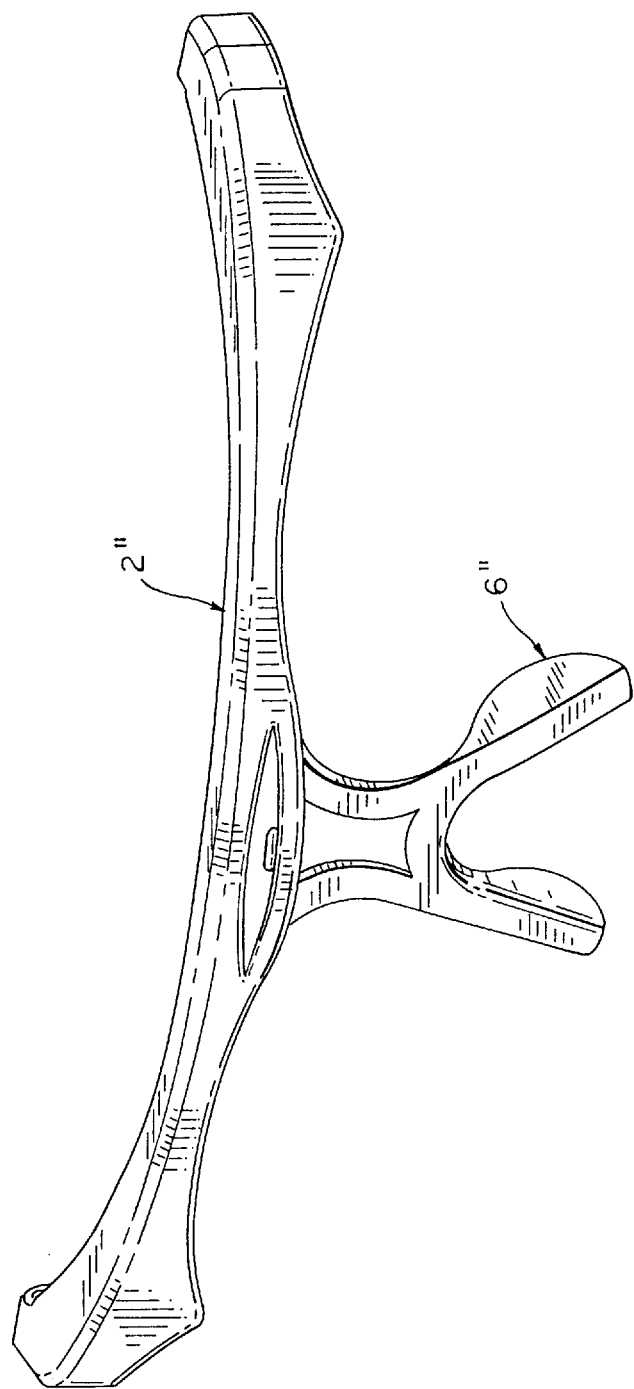
FIG. 9 is a perspective view of a modified embodiment of the frame.

FIG. 9 illustrates a modified embodiment of the frame 2", in which the nose piece 6" and the frame are integrally injection-molded, the nose piece 6" being mounted on the sight piece 1 together with the frame 2".

Figure 11:
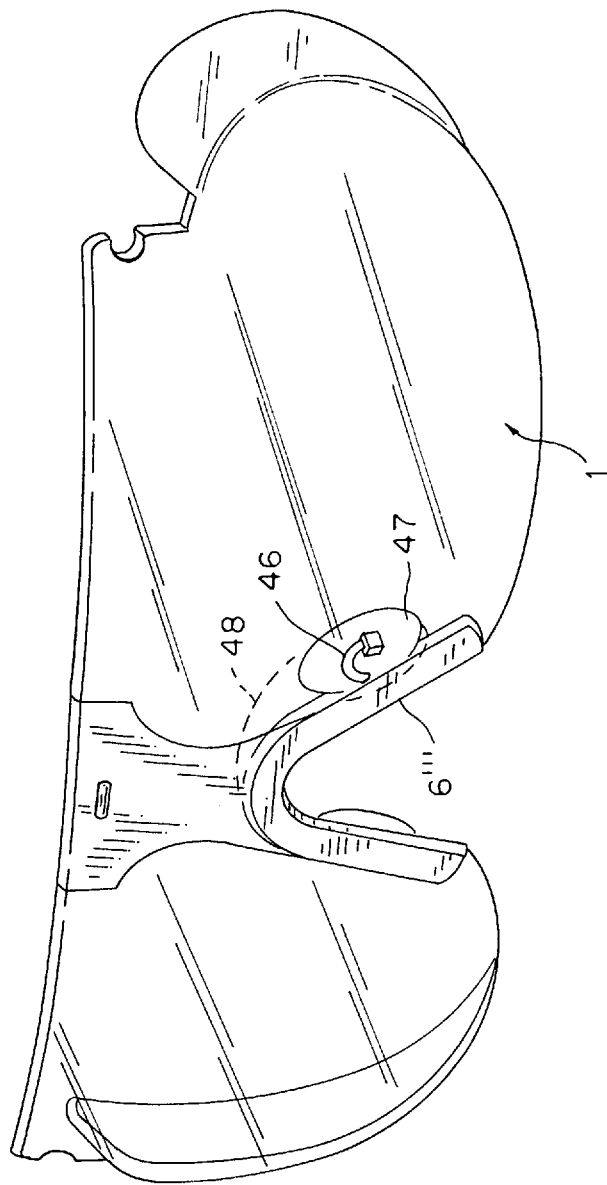
FIG. 11 is an illustration of the nose piece with the wire section incorporated by injection-molding.

FIG. 11 shows another modified embodiment. In this case, wires 46 to which nose pads 47 are fixed are incorporated in the nose piece 6''' by injection-molding. Nose pads 47 arranged on wires are not normally used in industrial safety goggles, however, combined with the one-piece sight piece and the advantages in terms of safety requirements of such a sight piece, they provide for optimal adaptation to a user's nose. Instead of nose pads 47, a nose loop can be fixed to the wires 46 as roughly outlined at 48 by a dashed line, i.e. a continuous part of plastic material extending between the wire sections over the nose of the user.

What is claimed is:

1. Safety goggles for an industrial user, comprising a one-piece sight piece, the sight piece having transparent, lateral pieces joined on, forming one piece with the sight piece and extending toward the head of the user, wherein the sight piece has a rounded configuration at lateral outer ends thereof and the lateral pieces joined on have a convexity that matches the rounded configuration wherein the rounded configuration of sight piece and the lateral pieces have an axis of curvature which extends in a direction towards the user's head and ears.

2. Safety goggles according to claim 1, wherein an average radius of curvature of the lateral pieces amounts to 1 cm to 3 cm.

3. Safety goggles according to claim 1, wherein a frame having lateral sections can be locked into place on an upper edge of the sight piece, and wherein articulated bows are respectively engaged to each of said lateral sections of the frame.

4. Safety goggles according to claim 3, wherein snap-in pieces can be respectively snapped in each of said lateral sections of the frame, the snap-in pieces each having hinge pieces for the respective articulation of each of said articulated bows.

5. Safety goggles according to claim 4, wherein an articulated piece on a side of each of said articulated bows is provided with a coupling section which can snap-engage with a bowed coupling piece.

6. Safety goggles according to claim 5, wherein the bowed coupling piece is of a plastic material that is softer than other pieces of the goggles.

7. Safety goggles according to claim 6, wherein the bowed coupling piece has an elongated slot with catching recesses for length adjustment, with which engages a locking projection on the inside of the articulated piece.

8. Safety goggles according to claim 3, wherein extreme ends of the frame enclose the snap-in piece in a form of a fork section, ribs being formed for inclination engagement on a front of each of said snap-in pieces and on a bight of a U formed by the forked section of each of said lateral sections.

9. Safety goggles according to claim 8, wherein the forked section comprises a stabilizing upper cover which prevents the snap-in piece from being detached.

10. Safety goggles according to claim 8, wherein a pivot bearing recess is formed in the forked section and a pivot bearing bolt is formed on one side of each snap-in piece and engages with the pivot bearing recess.

11. Safety goggles according to claim 10, wherein the pivot bearing bolt has a sloping face in a direction of insertion.

12. Safety goggles according to claim 3, wherein the frame has a cover section extending backward toward the face of a user.

13. Safety goggles according to claim 3, wherein on a lower side of the frame comprises a groove into which is inserted the upper edge of the sight piece, wherein the sight piece comprises recesses at lateral ends thereof, and wherein the frame comprises corresponding lateral holding arrangements for the sight piece to be arrested.

14. Safety goggles according to claim 13, wherein the holding arrangements are disposed on the frame, displaced downward in such a way that when the sight piece is inserted, the inner limiting wall of the groove which receives the upper edge of the sight piece fits over a portion of each of said holding arrangements.

15. Safety goggles according to claim 13, wherein the frame comprises a central catching recess for a locking projection disposed on an outside of the sight piece.

16. Safety goggles according to claim 1, wherein a wire section is incorporated into a nose piece by injection molding, lateral extreme ends of which run outward on both sides of the nose piece, nose pads and end sections of a nose loop being placed on said lateral extreme ends.

17. Safety goggles according to claim 1, wherein the sight piece is curved spherically.

18. Safety goggles according to claim 3, wherein holes for a holding strap are formed respectively on ends of said articulated bows.

19. Safety goggles according to claim 3, wherein a nose piece is formed on the frame by injection-molding.

20. Safety goggles according to claim 1, wherein the sight piece has plate-type pieces joined on and extending backward, in which oblong holes are formed, inclined relative to a horizontal, corresponding locking pieces on stems being formed on the inside of the frame, which can be inserted in the oblong holes and fixed by the frame being pivoted, the sight piece centrally having a locking projection and the frame a catching recess.

\* \* \* \* \*